United States Patent [19]

Jacobson

[11] Patent Number: 5,523,325
[45] Date of Patent: Jun. 4, 1996

[54] AMIDRAZONES AND THEIR USE AS PESTICIDES

[76] Inventor: Richard M. Jacobson, 11 Deerpath Rd., Chalfont, Pa. 18914

[21] Appl. No.: 118,915

[22] Filed: Sep. 9, 1993

[51] Int. Cl.$^6$ .................. C07C 327/56; C07C 251/80; A61K 31/165; A61K 31/15

[52] U.S. Cl. .............. 514/615; 514/238.5; 514/331; 514/428; 514/487; 514/512; 514/599; 544/163; 544/168; 546/231; 548/567; 558/248; 558/257; 558/262; 558/256; 560/27; 560/34; 564/74; 564/149; 564/150

[58] Field of Search ................... 564/149, 150, 564/74; 514/615, 238.5, 331, 428, 487, 512, 599; 544/163, 168; 546/231; 548/567; 556/248, 257, 262; 560/27, 34

[56] References Cited

U.S. PATENT DOCUMENTS

| | | | |
|---|---|---|---|
| 4,814,349 | 3/1989 | Addor et al. | 514/522 |
| 4,857,556 | 8/1989 | Yamada et al. | 514/585 |
| 4,954,655 | 9/1990 | Kelly | 564/464 |
| 4,985,461 | 1/1991 | Hsu et al. | 514/615 |
| 5,075,471 | 12/1991 | Michelotti et al. | 556/144 |
| 5,110,986 | 5/1992 | Kelly | 564/149 |
| 5,117,057 | 5/1992 | Hsu et al. | 564/150 |
| 5,225,443 | 7/1993 | Murphy et al. | 514/615 |
| 5,229,038 | 7/1993 | Uchino et al. | 252/582 |
| 5,278,180 | 1/1994 | Clemence et al. | 514/383 |

FOREIGN PATENT DOCUMENTS

| | | |
|---|---|---|
| 2015437 | 10/1990 | Canada . |
| 228564 | 7/1987 | European Pat. Off. . |
| 0361645 | 4/1990 | European Pat. Off. . |
| 234944 | 4/1991 | European Pat. Off. . |
| 483647 | 5/1992 | European Pat. Off. . |
| 245950 | 6/1992 | European Pat. Off. . |
| 496342 | 7/1992 | European Pat. Off. . |
| 261755 | 12/1992 | European Pat. Off. . |
| 347216 | 9/1993 | European Pat. Off. . |
| 176444 | 1/1994 | European Pat. Off. . |
| 1225800 | 10/1972 | Germany . |
| 1275554 | 11/1989 | Japan . |
| 3145447 | 6/1991 | Japan . |
| 4005203 | 1/1992 | Japan . |
| 4089471 | 3/1992 | Japan . |
| 417830 | 6/1992 | Japan . |
| 539252 | 2/1993 | Japan . |
| 2231268 | 11/1990 | United Kingdom . |

*Primary Examiner*—Peter O'Sullivan

[57] ABSTRACT

This invention relates to amidrazones, insecticidal amidrazone compositions, and methods of using such compositions.

11 Claims, No Drawings

AMIDRAZONES AND THEIR USE AS PESTICIDES

BACKGROUND OF THE INVENTION

This invention relates to amidrazones, insecticidal amidrazone compositions, and methods of using such compositions.

The search for compounds which have a combination of excellent insecticidal activity and low undersirable toxicity is a continuing one because of factors such as the desire for compounds exhibiting greater activity, better selectvity, low undesirable environmental impact, low production cost, and effectiveness against insects resistant to many known insecticides.

Compounds of the present invention have utility for controlling plant-destructive insects in crops of cultivated plants, ornamentals, and forestry.

SUMMARY OF THE INVENTION

In accordance with the present invention, there are provided compounds having the formula:

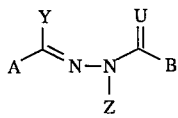

wherein

A is aryl or aromatic heterocyclyl;

B is aryl or aromatic heterocyclyl;

U is oxygen or sulfur;

Y is disubstituted amino (NRIR2);

wherein $R^1$ and $R^2$ are independently selected substituents or $R^1$ and $R^2$ together with the nitrogen to which they are attached may form a 5- or 6-membered ring; and Z is ($C_1$14 $C_9$)alkyl, branched ($C_3$–$C_9$)alkyl, or a (C1–C9)alkyl substituted with one or two of the same or different ($C_3$–$C_9$)cycloalkyl; and agronomically acceptable diastereomers and enantiomers of such compounds; and agronomically acceptable salts of such compounds.

Further, in accordance with the present invention, there are provided compositions containing compounds of the present invention and methods of using such compounds and compositions.

EMBODIMENTS OF THE INVENTION

In accordance with the present invention, there are provided compounds having the formula:

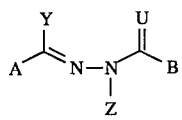

wherein

A is aryl or aromatic heterocyclyl;

B is aryl or aromatic heterocyclyl;

U is oxygen or sulfur;

Y is disubstituted amino ($NR^1R^2$);

wherein $R^1$ and $R^2$ are independently hydrogen, or a substituent selected from W; or R 1 and $R^2$ together with the nitrogen to which they are attached may form a 5- or 6-membered ring, preferably piperidino, morpholino, or pyrrolidino, each of piperidino, morpholino, or pyrrolidino being unsubstituted or substituted with at least one ($C_1$–$C_6$)alkyl; and Z is a straight or branched ($C_3$–$C_9$)alkyl, unsubstituted or substituted with one or two of the same or different ($C_3$–$C_9$)cycloalkyl; and agronomically acceptable diastereomers and enantiomers of such compounds; and agronomically acceptable salts of such compounds.

W is (alkanoylalkylthio)carbonyl, (alkenylthio)carbonyl, (alkylthio)carbonyl, (alkylthio)thiocarbonyl, (alkynylthio)carbonyl, (phenylalkylthio)carbonyl, alkanoylalkoxycarbonyl, alkanoyloxy, alkenyl, alkenylcarbonyl, alkenyloxy, alkenyloxycarbonyl, alkenylsulfonyl, alkenylthiocarbonyl, alkoxy, alkoxyalkoxy, alkoxyalkoxyalkoxycarbonyl, alkoxyalkoxyalkyl, alkoxyalkoxycarbonyl, alkoxyalkyl, alkoxyalkylcarbonyl, alkoxycarbonyl, alkoxycarbonyl(alkylthio)carbonyl, alkoxycarbonylalkoxycarbonyl, alkoxycarbonylalkyl, alkoxycarbonylalkylthio, alkoxycarbonylcarbonyl, alkoxycarbonyloxy, alkoxycarbonylthio, alkyl, alkylaminocarbonyl, alkylcarbonyl, alkylcarbonyl(alkylthio)carbonyl, alkylcarbonyloxyalkyl, alkylidenedioxy, alkylsulfinyl, alkylsulfinylalkyl, alkylsulfonyl, alkylsulfonyloxy, alkylthio, alkylthioalkoxycarbonyl, alkylthioalkyl, alkylthiocarbonyl, alkynyl, alkynylcarbonyl, alkynyloxy, alkynyloxycarbonyl, alkynylsulfonyl, amino, aromatic heterocyclyl, aryl, carboxy(alkylthio)carbonyl, carboxyalkoxycarbonyl, carboxyalkyl, cyano, cycloalkyl, dialkylphosphoryl, dialkylthiophosphoryl, formamido, formyl, formyloxy, halo, haloalkenyl, haloalkoxy, haloalkyl, halocarbonyl, heterocycyl, hydroxy, hydroxyalkyl, isocyano, N,N-dialkylamino, N,N-dialkylaminocarbonyl, N,N-dialkylaminocarbonylamino, N,N-dialkylaminocarbonyloxy, N,N-dialkylaminosulfonyl, N-(phenylcarbonyl)aminocarbonyl, N-alkoxycarbonyl-N-alkylamino, N-alkylaminocarbonyl, N-alkylaminosulfonyl, N-alkylcarbonyl-N-alkylamino, N-alkylcarbonylamino, N-formyl-N-alkylamino, N-formylamino, N-monoalkylamino, N-monoalkylaminocarbonyl, N-monoalkylaminocarbonylamino, N-monoalkylaminocarbonyloxy, N-monoalkylaminosulfonyl, N-phenyl-N-alkylaminocarbonyl, N-phenylcarbonylamino, naphthyl, nitro, phenyl, phenylalkenylcarbonyl, phenylalkoxy, phenylalkoxycarbonyl, phenylalkyl, phenylalkylcarbonyl, phenylalkylthiocarbonyl, phenylalkynylcarbonyl, phenylcarbonyl, phenyloxy, phenyloxycarbonyl, phenylsulfonyl, phenylthio, phenylthiocarbonyl, or pyridyloxy.

"(Alkanoylalkylthio)carbonyl" is ($C_1$–$C_6$)alkanoyl($C_1$–$C_6$))alkylthiocarbonyl, preferably (acetylmethylthio)carbonyl.

"(Alkenylthio)carbonyl" is (($C_3$–C6))alkenylthio)carbonyl, preferably (allylthio)carbonyl.

"(Alkylthio)carbonyl" is (($C_1$–$C_6$)alkylthio)carbonyl [e.g., ($C_1$–$C_6$)alkyl-S-C(=O)—], preferably (methylthio)carbonyl, (ethylthio)carbonyl, (n-propylthio)carbonyl, or (n-butylthio)carbonyl. "n-propyl" is normal propyl, i.e. straight chain propyl.

"(Alkylthio)thiocarbonyl" is (($C_1$–$C_6$))alkylthio)thiocarbonyl [e.g., ($C_1$–$C_6$)alkyl-S-C(=S)—], preferably (methylthio)thiocarbonyl.

"(Alkynylthio)carbonyl" is (($C_3$–$C_6$))alkynylthio)carbonyl, preferably (propargylthio)carbonyl.

"(Phenylalkylthio)carbonyl" is (phenyl($C_1$–$C_6$)alkylthio)carbonyl, preferably (benzylthio)carbonyl.

"Alkanoylalkoxycarbonyl" is ($C_1$–$C_6$)alkanoyl($C_1$–$C_6$)alkoxycarbonyl, preferably acetylmethoxycarbonyl.

"Alkanoyloxy" is ($C_1$–$C_6$)alkanoyloxy, preferably acetoxy.

"Alkenyl" is ($C_2$–$C_6$)alkenyl preferably vinyl and allyl.

"Alkenylcarbonyl" is ($C_2$–$C_6$)alkenylcarbonyl, preferably vinylcarbonyl, 1-methylvinylcarbonyl, 2-methylvinylcarbonyl, 2,2-dimethylvinylcarbonyl and 1,2,2-trichlorovinylcarbonyl.

"Alkenyloxy" is ($C_3$–$C6$)alkenyloxy, preferably allyloxy and but-3-enoxy.

"Alkenyloxycarbonyl" is ($C_3$–$C_6$)alkenyloxycarbonyl, preferably allyloxycarbonyl and but-3-enoxycarbonyl.

"Alkenylsulfonyl" is ($C_2$–$C_6$)alkenylsulfonyl, preferably vinylsulfonyl and allylsulfonyl.

"Alkenylthiocarbonyl" is ($C_3$–$C_6$)alkenylthiocarbonyl, preferably allylthiocarbonyl.

"Alkoxy" is ($C_1$–$C_6$)alkoxy, preferably methoxy, ethoxy, n-propoxy, isopropoxy, n-butoxy, sec-butoxy, isobutoxy, and t-butoxy.

"Alkoxyalkoxy" is ($C_1$–$C_6$)alkoxy($C_1$–$C_6$)alkoxy, preferably methoxymethoxy and 2-methoxyethoxy.

"Alkoxyalkoxyalkoxycarbonyl" is ($C_1$–$C_6$)alkoxy($C_1$–$C_6$)alkoxy($C_1$–$C_6$)alkoxycarbonyl, preferably 2-(2-(methoxy)ethoxy)ethoxycarbonyl.

"Alkoxyalkoxyalkyl" is ($C_1$–$C_6$)alkoxy($C_1$–$C_6$)alkoxy($C_1$–$C_6$)alkoxy, preferably 2-methoxyethoxymethyl.

"Alkoxyalkoxycarbonyl" is ($C_1$–$C_6$)alkoxy($C_1$–$C_6$)alkoxycarbonyl, preferably methoxyethoxycarbonyl.

"Alkoxyalkyl" is ($C_1$–$C_6$)alkoxy($C_1$–$C_6$)alkyl preferably methoxymethyl and 2-methoxyethyl.

"Alkoxyalkylcarbonyl" is ($C_1$–$C_6$)alkoxy($C_1$–$C_6$)alkylcarbonyl, preferably methoxymethylcarbonyl.

"Alkoxycarbonyl" is ($C_1$–$C_6$)alkoxycarbonyl, preferably methoxycarbonyl, ethoxycarbonyl, n-propyloxycarbonyl, isopropyloxycarbonyl, n-butyloxycarbonyl, isobutyloxycarbonyl, t-butyloxycarbonyl, n-pentyloxycarbonyl, cyanomethoxycarbonyl, 2-cyanoethoxycarbonyl, 2-bromoethoxycarbonyl, 2-chloroethoxycarbonyl, 2,2,2-trifluoroethoxycarbonyl, 2,2,2-trichloroethoxycarbonyl, 3-bromopropyloxycarbonyl, 3-chloropropyloxycarbonyl or 4-chlorobutyloxycarbonyl.

"Alkoxycarbonyl(alkylthio)carbonyl" is ($C_1$–$C_6$)alkoxycarbonyl(($C_1$–$C_6$)alkylthio)carbonyl, preferably (methoxycarbonylmethylthio)carbonyl.

"Alkoxycarbonylalkoxycarbonyl" is ($C_1$–$C_6$)alkoxycarbonyl, preferably ethoxycarbonylmethoxycarbonyl and ethoxycarbonylethoxycarbonyl.

"Alkoxycarbonylalkyl" is ($C_1$–$C_6$)alkoxycarbonyl($C_1$–$C_6$)alkyl preferably methoxycarbonylmethyl and ethoxycarbonylmethyl.

"Alkoxycarbonylalkylthio" is ($C_1$–$C_6$)alkoxycarbonyl(C 1–C6)alkylthio preferably methoxycarbonylmethylthio and ethoxycarbonylmethylthio.

"Alkoxycarbonylcarbonyl" is ($C_1$–$C_6$)alkoxycarbonylcarbonyl preferably methoxycarbonylcarbonyl and ethoxycarbonylcarbonyl.

"Alkoxycarbonyloxy" is ($C_1$–$C_6$)alkoxycarbonyloxy preferably methoxycarbonyloxy and ethoxycarbonyloxy.

"Alkoxycarbonylthio" is ($C_1$–$C_6$)alkoxycarbonylthio preferably methoxycarbonylthio and ethoxycarbonylthio.

"Alkyl" means straight and branched alkyl groups, and unless otherwise specified are preferably ($C_1$–$C_6$)alkyl, more preferably methyl, ethyl, n-propyl, isopropyl, n-butyl, isobutyl, s-butyl, t-butyl or n-pentyl.

"Alkylaminocarbonyl" is mono($C_1$–$C_6$)alkylaminocarbonyl, preferably methylaminocarbonyl, or di($C_1$–$C_6$)alkylaminocarbonyl, preferably dimethylaminocarbonyl.

"Alkylcarbonyl" is ($C_1$–$C_6$)alkylcarbonyl, preferably methylcarbonyl (acetyl), ethylcarbonyl, n-propylcarbonyl, isopropylcarbonyl, n-butylcarbonyl, isobutylcarbonyl, t-butylcarbonyl, n-pentylcarbonyl, chloromethylcarbonyl, trichloromethylcarbonyl, trifluoromethylcarbonyl, 3-chloropropylcarbonyl, 4-chlorobutylcarbonyl, pentafluoroethylcarbonyl or heptafluoropropylcarbonyl.

"Alkylcarbonyl(alkylthio)carbonyl" is ($_1$–$C_6$)alkylcarbonyl($C_1$–$C_6$)alkylthio)carbonyl preferably (methylcarbonylmethylthio)carbonyl.

"Alkylcarbonyloxyalkyl" is ($C_1$–$C_6$)alkylcarbonyloxy($C_1$–$C_6$)alkyl, preferably 2-(methylcarbonyloxy)ethyl or methylcarbonyloxymethyl.

"Alkylidenedioxy" is ($C_1$–$C_4$)alkylidenedioxy, preferably methylenedioxy and ethylenedioxy.

"Alkylsulfinyl" is ($C_1$–$C_6$)alkylsulfinyl preferably methylsulfinyl.

"Alkylsulfinylalkyl" is ($C_1$–$C_6$)alkylsulfinyl($C_1$–$C_6$)alkyl, preferably 2-(methylsulfinyl)ethyl.

"Alkylsulfonyl" is ($C_1$–$C_6$)alkylsulfonyl, preferably methylsulfonyl, n-butylsulfonyl, chloromethylsulfonyl, trifluoromethylsulfonyl or 2,2,2-trifluoroethylsulfonyl.

"Alkylsulfonyloxy" is ($C_1$–$C_6$)alkylsulfonyloxy preferably methylsulfonyloxy.

"Alkylthio" is ($C_1$–$C_6$)alkylthio, preferably methylthio, n-propylthio, n-butylthio or 3-cyanopropylthio.

"Alkylthioalkoxycarbonyl" is ($C_1$–$C_6$)alkylthio($C_1$–$C_6$)alkoxycarbonyl, preferably methylthiomethoxycarbonyl.

"Alkylthioalkyl" is ($C_1$–$C_6$)alkylthio($C_1$–$C_6$)alkyl, preferably methylthiomethyl, 2-(methylthio)ethyl or 2-(ethylthio)ethyl.

"Alkylthiocarbonyl" is ($C_1$–$C_6$)alkylthiocarbonyl preferably thioacetyl.

"Alkynyl" is ($C_1$–$C_6$)alkynyl preferably propargyl, and but-2-yn-1-yl.

"Alkynylcarbonyl" is ($C_1$–$C_6$)alkynylcarbonyl preferably propargylcarbonyl.

"Alkynyloxy" is ($C_3$–$C_6$)alkynyloxy, preferably propargyloxy and but-3-ynoxy.

"Alkynyloxycarbonyl" is ($C_3$–$C_6$)alkynyloxycarbonyl, preferably propargyloxycarbonyl.

"Alkynylsulfonyl" is ($C_3$–$C_6$)alkynylsulfonyl, preferably propargylsulfonyl.

"Aromatic Heterocyclyl" is a fully unsaturated five or six membered heterocyclic ring containing one, two or three heteroatoms independently selected from oxygen, nitrogen or sulfur with the remaining ring atoms being carbon atoms. Preferred are furyl, pyridyl, pyrazinyl, pyrimidinyl, triazinyl, oxazolyl, pyrrazolyl, imidazolyl, triazolyl, thienyl, and thiazolyl. The heterocycyl ring is optionally substituted by one or two substituents independently selected from W. Preferably nitro; ($C_1$–$C_6$)alkyl, preferably methyl or ethyl; ($C_1$–$C_6$)haloalkyl, preferably trifluoromethyl; ($C_1$–$C_6$)alkoxy, preferably methoxy; and halo, preferably chloro.

"Aryl" is an aromatic ($C_6$–$C_{16}$)carbocyclic structure, preferably an unsaturated monocyclic or bicyclic($C_6$–$C_1$)carbocyclic structure, more preferably phenyl or naphthyl. The aryl group is optionally substituted by one or two substituents independently selected from W. Preferably nitro; ($C_1$–$C_6$)alkyl, preferably methyl or ethyl; ($C_1$–$C_6$)haloalkyl, preferably trifluoromethyl; ($C_1$–$C_6$)alkoxy, preferably methoxy; and halo, preferably chloro.

"Carboxy(alkylthio)carbonyl" is carboxy(($C_1$–$C_6$)-alkylthio)carbonyl, preferably carboxy(methylthio)carbonyl "Carboxyalkoxycarbonyl" is carboxy($C_1$–$C_6$)alkoxycarbonyl, preferably carboxyethoxycarbonyl or carboxypropoxycarbonyl.

"Carboxyalkyl" is carboxy($C_1$–$C_6$)alkyl, preferably carboxymethyl.

"Cycloalkyl" means ($C_3$–$C_{12}$) carbocyclic structures and alkyl substituted carbocycles such as cyclopropyl, cyclobutyl, cyclopentyl, cyclohexyl and menthyl.

"Dialkylphosphoryl" is di($C_1$–$C_6$)alkylphosphoryl, preferably diethylphosphoryl.

"Dialkylthiophosphoryl" is di($C_1$–$C_6$)alkylthiophosphoryl, preferably diethylthiophosphoryl.

"Halo" means bromo, chloro, fluoro and iodo; "halogen" is bromide, chloride, fluoride and iodide.

"Haloalkenyl" is ($C_2$–$C_6$)alkenyl, preferably 2,2-dibromovinyl, 2,2-dichlorovinyl, 2,2-difluorovinyl or 2-bromovinyl.

"Haloalkoxy" is halo($C_1$–$C_6$)alkoxy, preferably trifluoromethoxy, difluoromethoxy, 1,1,2,2-tetrafluoroethoxy or 1,1,2,3,3,3-hexafluoropropyloxy.

"Haloalkyl" is halo($C_1$–$C_6$)alkyl, preferably trifluoromethyl, 2-chloroethyl or 2-bromoethyl.

"Halocarbonyl" is preferably chlorocarbonyl.

"Heterocycyl" is a fully saturated, partly unsaturated, or fully unsaturated five or six membered heterocyclic ring containing one, two or three heteroatoms independently selected from oxygen, nitrogen or sulfur with the remaining ring atoms being carbon atoms. Preferred are piperidyl, morpholinyl, tetrahydrofuranyl, pyrrolidinyl, furyl, pyridyl, pyrazinyl, pyrimidinyl, triazinyl, oxazolyl, pyrrazolyl, imidazolyl, triazolyl, thienyl, and thiazolyl. The heterocycyl ring is optionally substituted by one or two substituents independently selected from W. Preferably nitro; ($C_1$–$C_6$)alkyl, preferably methyl or ethyl; ($C_1$–$C_6$)haloalkyl, preferably trifluoromethyl; ($C_1$–$C_6$)alkoxy, preferably methoxy; and halo, preferably chloro.

"Hydroxyalkyl" is hydroxy($C_1$–$C_6$)alkyl, preferably hydroxymethyl, 1-hydroxyethyl or 2-hydroxyethyl.

"N,N-dialkylamino" is N,N-di($C_1$–$C_6$)alkyl,amino, preferably dimethylamino or diethylamino.

"N,N-dialkylaminocarbonyl" is N,N-di($C_1$–$C_6$)alkylaminocarbonyl preferably dimethylaminocarbonyl.

"N,N-dialkylaminocarbonylamino" is N,N-di($C_1$–$C_6$)alkylaminocarbonylamino, preferably dimethylaminocarbonylamino.

"N,N-dialkylaminocarbonyloxy" is N,N-di($C_1$–$C_6$)alkylaminocarbonyloxy, preferably dimethylaminocarbonyloxy.

"N,N-dialkylaminosulfonyl" is N,N-di($C_1$–$C_6$)alkylaminosulfonyl, preferably dimethylaminosulfonyl.

"N-(phenylcarbonyl)aminocarbonyl" is preferably N-(2,6-difluorophenylcarbonyl)aminocarbonyl.

"N-Alkoxycarbonyl-N-alkylamino" is N-($C_1$–$C_6$)alkoxycarbonyl-N-($C_1$–$C_6$)alkylamino, preferably N-methoxycarbonyl-N-methylamino, N-methoxycarbonyl-N-propylamino, and N-ethoxycarbonyl-N-ethylamino.

"N-alkylaminocarbonyl" is N-($C_1$–$C_6$)alkylaminocarbonyl, preferably methylaminocarbonyl.

"N-alkylaminosulfonyl" is N-($C_1$–$C_6$)alkylaminosulfonyl, preferably N-methylaminosulfonyl.

"N-alkylcarbonyl-N-alkylamino" is N-($C_1$–$C_6$)alkylcarbonyl- N-($C_1$–$C_6$)alkylamino, preferably N-acetyl-N-methylamino, N-ethylcarbonyl-N-propylamino, and N-propylcarbonyl-N-ethylamino.

"N-Alkylcarbonylamino" is N-($C_1$–$C_6$)alkylcarbonylamino, preferably acetylamino "N-formyl-N-alkylamino" is N-formyl-N-($C_1$–$C_6$)alkylamino, preferably N-formyl-N-methylamino and N-formyl-N-propylamino.

"N-monoalkylamino" is N-mono($C_1$–$C_6$)alkylamino, preferably N-methylamino.

"N-monoalkylaminocarbonyl" is N-mono($C_1$–$C_6$)alkylaminocarbonyl, preferably N-methylaminocarbonyl "N-monoalkylaminocarbonylamino" is N-mono($C_1$–$C_6$)alkylaminocarbonylamino, preferably N-methylaminocarbonylamino.

"N-monoalkylaminocarbonyloxy" is N-mono($C_1$–$C_6$)alkylaminocarbonyloxy, preferably N-methylaminocarbonyloxy.

"N-monoalkylaminosulfonyl" is N-mono($C_1$–$C_6$)alkylaminosulfonyl, preferably N-methylaminosulfonyl "N-phenyl-N-alkylaminocarbonyl" is N-phenyl-N-($C_1$–$C_6$)alkylaminocarbonyl, preferably N-methyl-N-(phenyl)aminocarbonyl.

"N-phenylcarbonylamino" is preferably N-(4-chlorophenyl)carbonylamino.

"Naphthyl" is naphthyl optionally substituted by one or two substituents independently selected from W. Preferably nitro; ($C_1$–$C_6$)alkyl, preferably methyl or ethyl; ($C_1$–$C_6$)haloalkyl, preferably trifluoromethyl; ($C_1$–$C_6$)alkoxy, preferably methoxy; and halo, preferably chloro.

"Phenyl" is phenyl optionally substituted by one to three substituents independently selected from W. Preferred substituents are methyl, ethyl, propyl, t-butyl, trifluoromethyl, dichloromethyl, trichloromethyl, fluoro, bromo, chloro, iodo, hydroxy, methoxy, ethoxy, n-propyloxy, isopropyloxy, sec-butyloxy, n-butyloxy, isobutyloxy, n-pentyloxy, difluoromethoxy, trifluoromethoxy, 1,1,2,2-tetrafluoroethoxy, bromodifluoromethoxy, 1,1,2,3,3,3-hexafluoropropyloxy, allyloxy, propargyloxy, methoxymethoxy, benzyloxy, 2-phenylethoxy, phenyloxy, 2-chloro-4-trifluoromethylphenyloxy, 5ochloro-2-Pyridyloxy, 5-(trifluoromethyl)-2-pyridyloxy, 3-chloro-5-(trifluoromethyl)-2-pyridyloxy, methylaminocarbonyloxy, N,N-dimethylaminocarbonyloxy, acetoxy, methoxycarbonyloxy, methylsulfonyloxy, trifluoromethylsulfonyloxy, methylthio, 1,1,2,2,tetrafluoroethylthio, 2-ethoxyethyl, acetyl, (i.e., methylcarbonyl), ethylcarbonyl, isopropylcarbonyl, methoxycarbonyl, ethoxycarbonyl, isopropyloxycarbonyl, nitro, methylsulfonyl, 1,1,2,2-tetrafluoroethylsulfonyl, phenyl, cyano, isocyano, amino, methylamino, dimethylamino, formylamino, acetamido, trifluoroacetamido, phenylcarbonylamino, 4-chlorophenylcarbonylamino, methylaminocarbonylamino, and di-n-propylaminocarbonylamino. The preferred positioni on the phenyl is is the 4positioin; for example, the preferred methylphenyl is 4-methylphenyl.

"Phenylalkenylcarbonyl" is phenyl($C_2$–$C_6$)alkenylcarbonyl, preferably phenylvinylcarbonyl (cinnamoyl).

"Phenylalkoxy" is ($C_7$–$C_{11}$)phenylalkoxy, preferably benxyloxy and 3-phenylpropoxy.

"Phenylalkoxycarbonyl" is phenyl($C_1$–$C_6$)alkoxycarbonyl, preferably benzyloxycarbonyl or 2-phenylethoxycarbonyl.

"Phenylalkyl" is phenyl($C_1$–$C_6$)alkyl, preferably benzyl or 2-phenylethyl.

"Phenylalkylcarbonyl" is phenyl($C_1$–$C_6$)alkylcarbonyl.

"Phenylalkylthiocarbonyl" is phenyl($C_1$–$C_6$)alkylthiocarbonyl.

"Phenylalkynylcarbonyl" is phenyl($C_2$–$C_6$)alkynyl.

"Phenylcarbonyl" is unsubstituted phenylcarbonyl or substituted phenyl, preferably 4-chlorophenylcarbonyl, 4-methylphenylcarbonyl or 4-trifluoromethylphenylcarbonyl.

"Phenyloxy" is preferably phenoxy or 4-chlorophenoxy.

"Phenyloxycarbonyl" is preferably phenoxycarbonyl or 4chlorophenoxycarbonyl.

"Phenylsulfonyl" is preferably phenylsulfonyl or 4-methylphenylsulfonyl.

"Phenylthio" is unsubstituted phenylthio and substituted phenylthio, preferably 2-nitro phenylthio.

"Phenylthiocarbonyl" is ($C_6$–$C_{10}$)phenylthiocarbonyl, preferably phenylthiocarbonyl and 4-chlorophenylthiocarbonyl.

"Pyridyloxy" is preferably 2-pyridyloxy, 5-chloro-2-pyridyloxy, 5-trifluoromethyl-2- pyridyloxy, or 3-chloro-5-trifluoromethyl-2-pyridyloxy.

erably one to two, substituents independently selected from halogens, preferably bromo, alkoxys, preferably methoxy, and alkyls, preferably methyl or ethyl. Preferably A is 4-substituted phenyl, more preferably 4-bromophenyl or 4-ethylphenyl. Preferably B is phenyl or 3,5-dimethylphenyl. Also in this preferred embodiment, Z is a branched ($C_4$–$C_7$)alkyl, preferably tert-butyl, tert-amyl, or neo-pentyl; U is oxygen or sulfur, preferably oxygen; and Y is 1-morpholino, 1-piperidino or di($C_1$–$C_3$)alkylamino, preferably dimethylamino. Accordingly, a preferred compound is a compound wherein A and B are each phenyl independently optionally substituted by one to three substituents independently selected from halogens, methyl and ethyl, Z is a branched ($C_4$–$C_7$)alkyl, U is oxygen, and Y is 1-morpholino, 1-piperidino, or di($C_1$–$C_3$)alkylamino. Preferred compounds are N-(4-bromobenzoyl)-morpholine $N^2$-benzoyl-$N^2$-t-butylhydrazone; N-(4-bromobenzoyl)-morpholine $N^2$-(3,5-dimethylbenzoyl)-$N^2$-t-butylhydrazone; N-benzoyl)-dimethylamino $N^2$-(3,5-dimethylbenzoyl)-$N^2$-t-butylhydrazone; N-(4-ethylbenzoyl)-morpholine $N^2$-(3,5-dimethylbenzoyl)-$N^2$-t-butylhydrazone; N-(4-ethylbenzoyl)-piperidine $N^2$-(3,5-dimethylbenzoyl)-$N^2$-t-butylhydrazone; N-(4-ethylbenzoyl))-pyrrolidine $N^2$-(3,5-dimethylbenzoyl)-$N^2$-t-butylhydrazone; and N-(4-ethylbenzoyl)-amine $N^2$-(3,5-dimethylbenzoyl)-$N^2$-t-butylhydrazone.

The following table lists examples of compounds of the present invention, but are not intended as limitations on the invention.

TABLE I

| Example # | A | B | Y | Z | U |
|---|---|---|---|---|---|
| 1 | 4-bromophenyl | phenyl | 1-morpholino | t-butyl | O |
| 2 | 4-bromophenyl | 3,5-dimethylphenyl | 1-morpholino | t-butyl | O |
| 3 | 4-ethylphenyl | 3,5-dimethylphenyl | dimethylamino | t-butyl | O |
| 4 | 4-ethylphenyl | 3,5-dimethylphenyl | 1-morpholino | t-butyl | O |
| 5 | 4-ethylphenyl | 3,5-dimethylphenyl | 1-piperidino | t-butyl | O |
| 6 | 4-ethylphenyl | 3,5-dimethylphenyl | 1-pyrrolidino | t-butyl | O |
| 7 | 4-ethylphenyl | 3,5-dimethylphenyl | amino | t-butyl | O |

"Agronomically acceptable salts" include acid addition salts, preferably hydrochloride, sulfate, and bisulfate; metal salts, preferably sodium, potassium, calcium and magnesium; ammonium salts, preferably isopropylammonium; and trialkylsulfonium salts, preferably trimethylsulfonium.

"Pesticidally effective amount" means the amount of active substance sufficient to exert the desired pest control, preferably causing a significant reduction compared to a control group of either the pest population or crop damage inflicted by such pest population, more preferably causing a twenty-five percent reduction, even more preferably at least ninety percent reduction.

In certain cases the compounds of this invention possess asymmetric centers which give rise to optical enantiomorphs and diastereomers. The compounds may also possess acidic or basic moieties which may form salts or metal complexes; this invention includes such enantiomorphs, salts and metal complexes.

In one preferred embodiment, A and B are each phenyl independently optionally substituted by one to three, pref- The compositions and compounds of this invention can be applied directly to the locus to be protected, as for example, the area around or upon economic plants infected with insects or to plants on which infestation is to be prevented. The compounds and compositions may be used either as contact or systemic pesticides.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as "systemic" application. Alternatively, the active compound may be applied to the soil and contacted therein with the insects and other pests to be controlled. This means of application is referred to as "soil" application. In another alternative, the active compound may be foliarly applied to the plants to be freed from insects and other pests which feed on the foliage.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. An agronomically acceptable carrier is any substance which can be used to dissolve, disperse or diffuse the active ingredient in the composition without impairing the active ingredients effectiveness and which by itself has no significant detrimental effect on the soil, equipment, desirable plants, or agronomic environment. If desired, adjuvants such as surfactants, stabilizers, antifoam agents and antidrift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. Baits are preparations generally comprising a food or other substance attractive to insects, that includes at least one compound of the instant invention. The invert emulsions are mainly used for air application, where large areas are treated with a comparatively small amount of preparation and may be prepared in the spraying apparatus shortly before, or even during, the spraying operation by emulsifying water in an oil solution or an oil dispersion of the active substance.

Compositions and formulations are prepared in a known manner, for instance by extending the active compounds with conventional pesticide dispersible liquid diluent carriers and/or dispersible solid carriers optionally with the use of carrier vehicle assistants such as conventional pesticide surface-active agents, including emulsifying agents and/or dispersing agents when water is used as diluent, organic solvents may be added as auxiliary solvents.

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001–99% by weight. For compositions suitable for storage or transportation, the amount of active ingredient is preferably between about 0.5–90% by weight, and more preferably between about 1–75% by weight of the mixture. Compositions suitable for direct application or field application generally contain the active compound in an amount substantially between about 0.0001–95%, preferably between about 0.0005–90% by weight, and more preferably between about 0.001–75% by weight of the mixture.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combatting or controlling pests which compromises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added adhesives such as polyvinylalcohol-cellulose derivatives or other colloidal materials, such as casein, to improve the adherence of the pesticide to the surface to be protected.

Compositions and formulations according to the present invention may also include known pesticidal compounds. The following known insecticidal, fungicidal and acaricidal compounds are suitable for use in such a combined preparation: acephate, acethion, acetoxon, aldicarb, aldoxycarb, aldrin, allethrin, allyxycarb, alphacypermethrin, amidithion, amitraz, amlure, anethol, azethion, azinphos-ethyl, azinphos-methyl, azocyclotin, bacillus thuringiensis, BCPE, bendiocarb, bensultap, benzoximate, benzyl acetate, benzyl benzoate, BHC, bifenthrin, binapacryl, bomyl, BPMC, bromophos, bromophos-ethyl, bromopropylate, bufencarb, buprofezin, butacarb, butocarboxim, butonate, butoxycarboxim, calcium arsenate, carbaryl, carbofuran, carbophenothion, carbosulfan, cartap, chlordane, chlordecone, chlordimeform, chlorfenethol, chlorfenson, chlorfensulphide, chlorfenvinphos, chlormephos, chlorobenzilate, chloropropylate, chlorphoxim, chlorpyrifos, chlorpyrifos methyl, chlorthiophos, clofentezine, CPCBS, CPMC, crotoxyphos, crufomate, cryolite, cufraneb, cyanofenphos, cyanophos, cyanthoate, cyfluthrin, cyhexatin, cypermethrin, cyphenothrin, cyromazine, DAEP, DDT, DDVP, deltamethrin, demeton, demeton-S-methyl, demeton-O-methyl, demeton-S, demeton-S-methyl sulfoxid, demephion-O, demephion-S, dialifor, diazinon, dicapthon, dichlofenthion, dicofol, dicrotophos, dieldrin, dienochlor, diflubenzuron, dihydrorotenone, dimefox, dimetan, dimethoate, dimethrin, dinex, dinitrophenol, dinobuton, dinocap, dioxabenzofos, dioxacarb, dioxathion, disparlure, disulfoton, DMCP, DNOC, d-trans allethrin, endosulfan, endothion, endrin, entice, EPBP, EPN, esfenvalerate, ethiofencarb, ethion, ethoatemethyl, ethoprop, etrimfos, fenamiphos, fenazaflor, fenbutatin-oxide, fenitrothion, fenoxycarb, fenpropathrin, fenson, fensulfothion, fenthion, fenvalerate, flubenzimine, flucythrinate, fluenethyl, flufenoxuron, fluvalinate, fonofos, formetanate hydrochloride, formothion, fosmethilan, fosthietan, furathiocarb, furethrin, grandlure, heptachlor, HETP, hexythiazox, hydramethylnon, hydroprene, IPSP, isazophos, isobenzan, isofenphos, isoprocarb, isoprothiolane, isothioate, isoxathion, jodfenphos, kinoprene, lead arsenate, leptophos, lethane, lindane, lythidathion, malathion, mazidox, mecarbam, mecarphon, menazon, mephosfolan, methamidophos, methidathion, methiocarb, methomyl, methoprene, methoxychlor, methyl parathion, methyl phencapton, mevinphos, mexacarbate, MIPC, mirex, monocrotophos, MTMC, naled, nicotine, nonachlor, omethoate, ovex, oxamyl, oxydeprofs, oxydisulfoton, oxythioquinox, paraoxon, parathion, paris green, permethrin, perthane, phencapton, phenthoate, phorate, phosalone, phosfolan, phosmet, phosnichlor, phosphamidon, phoxim, pirimicarb, pirimiphos-ethyl, pirimiphos-methyl, plifenate, profenofos, promecarb, propargite, propetamphos, propoxur, prothidathion, prothiophos, prothoate, PTMD, pyridaben, pyridaphenthion, quinalphos, resmethrin, ronnell, rotenone, ryania, s-bioallethrin, salithion, schradan, sodium fluosilicate, sophamide, sulfotepp, sulprofos, tefluthrin, temephos, TEPP, terbufos, tetrachlorvinphos, tetradifon, tetramethrin, tetrasul, thallium sulfate, thiocarboxime, thiocyclam-hydrogenoxalate,thiometon, tolclofos-methyl, toxaphene, triazophos, trichlorfon, trichloronate, triflumuron, trimethacarb, vamidothion, xylylcarb.

Fungicides which can be combined with the insecticides of this invention also include:

(a) dithiocarbamate and derivatives such as ferbam, ziram, maneb, mancozeb, zineb, propineb, metham, thiram, the complex of zineb and polyethylene thiuram disulfide, dazomet, and mixtures of these with copper salts;

(b) nitrophenol derivatives such as dinocap, binapacryl, and 2-sec-butyl-4,6-dinitrophenyl isopropyl carbonate;

(c) heterocyclic structures such as captan, folpet, glyodine, anilazine, ditalimfos, 4-butyl-1,2,4-triazole, 5-amino-l-[bis(dimethylamino)phosphinyl]-3-phenyl-1,2,4-triazole, etradiazole, dithianon, thioquinox, benomyl, thiabendazole, 4-(2-chlorophentylhgydrazono)-3-methylo5-isoxazolone, vinclozolin, iprodione, procymidone, triadimenol, triadimefon, bitertanol, prochloraz, fenasimol, bis-(p-chlorophenyl)-3pyridinemethanol, bis-(p-chlorophenyl)-5-pyrimidinemethanol, triarimol, flutriafol, flusilazole, propiconazole, ectaconazole, myclobutanil, alpha-[2-(4-chlorophenyl)ethyl]-alpha-phenyl-1H-1,2,4-triazole-l-propanenitrile, hexaconazole, cyproconazole, terbuconazole, diniconazole, fluoroimide, pyridine-2-thiol-l-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[( 1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N(2'-methoxyacetyl)alanine methyl ester, D,L-methyl-N-(2,6-dimethylphenyl)-N-chloroacetyl-D,L-2-aminobutyrolactone, D,L-N-(2,6-dimethylphenyl)-N(phenylacetyl)alanine methyl ester, 5-methyl-5-vinyl-3-(3,5-dichlorophenyl)-2,4-dioxo- 1,3-oxazolidine, 3-(3,5-dichlorophenyl)-5-methyl-5-(methoxymethyl)-1,3-oxazolidi-2,4-dione, 3-(3,5-dichlorophenyl)-l-isopropylcarbamoylhydantoin, 2-cyano-[N-(ethylaminocarbonyl)-2-methoximino] acetamide, fenpropimorph, fenpropidine, 2,6-dimethyl-N-tridecylmorpholine, dodemorph, and triforine;

(d) miscellaneous halogenated fungicides such as chloranil, dichlone, chloroneb, tricamba, TCPN, dichloran, 2-chloro-l-nitropropane, polychloronitrobenzenes such as pentachloronitrobenzene (PCNB), and tetrafluorodichloroacetone;

(e) fungicidal antibiotics such as griseofulvin, kasugamycin, polyoxin, validamycin, and streptomycin;

(0 copper-based fungicides such as copper hydroxide, cuprous oxide, basic cupric chloride, basic copper carbonate, copper terephthalate, copper naphthenate and Bordeaux mixture; and (g) miscellaneous fungicides such as dodine, phenylmercuric acetate, N-ethylmercuri-1,2,3,6-tetrahydro-3,6-endom ethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, thiophanate-methyl, flutolanil, edinophos, isoprothiolane, propenazole, and tricyclazole.

The compounds of this invention may be prepared by a variety of reaction schemes. The following examples exemplify preparation of the intermediate and final compounds of Table I above, but are not intended to be limits thereon.

EXAMPLE A

Preparation of the intermediate $N^1$-t-butyl-$N^1$-(3,5-dimethylbenzoyl)hydrazine To a 3 liter flask fitted with mechanical stirring and a reflux condensor is charged 160 g (1.28 mole) t-butyl hydrazine hydrochloride, 160 ml (8.89 mole) of water and 108 g (1.35 mole) of 50% sodium hydroxide solution in water. Slowly 100 g (1.72 mole) acetone is added and stirred 1 hour. The reaction mixture is diluted with 600 ml methylene chloride and followed by a careful addition of a mixture of 120 g (1.5 mole) 50% sodium hydroxide in 120 of ice. To the reaction mixture is then added 169 g (1.0 mole) of 3,5-dimethylbenzoyl chloride dropwise over 1.75 hours and stirred an additional hour. 500 ml of water containing 5 ml of concentrated hydrochloric acid ier and 108 g (1.35 mole) of 50% sodium hydroxidis transferred to a separatory funnel, washed twice more with 300 ml water each, dried over anhydrous magnesium sulfate, and concentrated in vacuo to yield 298 g (1.14mole) of a pale yellow oil.

The 298 g of pale yellow oil isolated above, 600 ml of toluene, 400 ml of water and 5.0 g (0.056 mole) of oxalic acid are charged to a 3 liter flask fitted with a mechanical stirrer and Dean Stark trap and refluxed 5 hours. During this time fresh toluene and water are added to replace that lost by draining the Dean Stark trap. The reaction mixture is neutralized with dilute sodium hydroxide and washed with brine one time quickly. The product, which precipitated upon cooling to room temperature, is filtered and triturated with hexanes. Obtained is 153 g of white solid, mp 125°–127° C.

EXAMPLE B

Preparation of N-(4-bromobenzoyl)-morpholine $N^2$-benzoyl-$N^2$-t-butylhydrazone a: N-(4-bromothiobenzoyl)-morpholine To 40 g (460 mmole) of morpholine is added 18.56 g (100 mmole) of 4-bromobenzaldehyde and 4.08 g (125 mmole) of elemental sulfur. The solution is refluxed for 15 minutes. The reaction mixture is poured onto water and extracted with 1 liter of ethyl acetate. The ethyl acetate extract is washed with brine, dried over anhydrous magnesium sulfate, evaporated in vacuo, then triturated with ethyl ether/hexanes to yield 26.9 g of the product, mp 135°–137° C.

b: 1-(4-bromobenzoyl)-morpholine $N^2$-t-butylhydrazone

To 5.0 g (18.7 mmole) of N-(4-bromothiobenzoyl)-morpholine prepared in Example B.a is added 12.5 g (142 mmole) of anhydrous t-butyl hydrazine. The mixture is heated at reflux (bath temp. ~160° C.) for 6 hours, stirred at room temperature over the weekend, then refluxed for an additional 8 hours. The reaction is cooled to room temperature, diluted with methylene chloride and washed with water. The methylene chloride solution is dried over anhydrous magnesium sulfate, evaporated in vacuo and triturated with ethyl ether/hexanes. The soluble fraction contained the product contaminated with ~10% starting material.

c: N-(4-bromobenzoyl)-morpholine $N^2$-benzoyl-$N^2$-t-butylhydrazone

To 2.0 g (6.2 mmole) of 1-(4-bromobenzoyl)-morpholine $N^2$-t-butylhydrazone in 15 g of methylene chloride is added 0.5 g (6.0 mmole) of anydrous sodium bicarbonate, 10 ml (6.0 mmole) of 5% sodium bicarbonate solution in water, and 0.95 g (6.8 mmole) of benzoyl chloride. The two phase solution is stirred 15 minutes at room temperature, separated, dried over anhydrous magnesium sulfate then evaporated in vacuo. The crude product crystallized out of hexanes at −5° C. and is chromatographed on silica in 1:1 ethyl ether/hexanes to yield the desired product, mp 119°–121° C.

Example C

Preparation of N-(4-bromobenzoyl)-morpholine $N^2$-(3,5-dimethylbenzoyl)-$N^2$-t-dimethylbenzoyl)-$N^2$-t- butylhydrazone By substantially following the procedure of Example B, using 3,5-dimethyl benzoyl chloride in place of benzoyl chloride, one obtains 2.0g of the desired product, an oil. nmr $(CDC_3)$ δ5 1.4 9H s, 2.3 6H s, 3.2 4H bs, 3.6 4H m, 6.6–7.5 7H m.

EXAMPLE D

Preparation of N,N-dimethylbenzamide $N^2$-(3,5-dimethylbenzoyl)-$N^2$-t-butylhydrazone a: N,N-dimethyl-4-ethylbenzamide In 50 g of water is dissolved 36.0 g (442 mmole) of dimethylamine hydrochloride. 50 g of ice and 36 g (450 mmole) of 50% sodium hydroxide solution are added. While maintaining the internal temperature below 10° C, 35 g (208 mmole) of 4-ethylbenzoyl chloride is added. The mixture is stirred 20 minutes, extracted with ethyl ether, dried over anhydrous magnesium sulfate and concentrated in vacuo to yield 36.2 g of N,N-dimethyl-4-ethylbenzamide.

b: N,N-dimethylimmonium-4-ethylbenzoyl chloride chloride 3.5 g (19.8 mmole) of N,N-dimethyl-4-ethylbenzamide prepared in Example D.a and 3.0 g (25 mmole) of thionyl chloride are dissolved in 6 g of methylene chloride and refluxed 4 hours. The reaction mixture is evaporated in vacuo and triturated with ethyl ether/hexanes to yield 2.5 g of product.

c: N-(benzoyl)-dimethylamino $N^2$-(3,5-dimethylbenzoyl)-$N^2$-t-butylhydrazone

In 10 ml of methylene chloride are dissolved 2.5 g (10.8 mmole) of N,N-dimethylimmonium-4-ethylbenzoyl chloride chloride obtained in Example 3b and 2.5 g (11.4 mmole) of $N^1$-t-butyl-$N^1$-(3,5dimethylbenzoyl)-hydrazine obtained from Example A. Upon adding 2.5 g (24.7 mmole) of triethylamine dropwise an exotherm is observed. The reaction is stirred 30 minutes, concentrated in vacuo and partitioned between ethyl ether and 1M sodium hydroxide solution. The ethyl ether layer is dried over anhydrous magnesium sulfate, concentrated and chromatographed on silica gel in 1:1 ethyl ether:hexanes yielding 2.0 g of an oil. nmr $(CDC_{13})$δ1.2 3H t, 1.4 9H s, 2.3 6H s, 2.6 2H q, 2.8 6H s, 6.6–7.2 7H m.

EXAMPLE E

Preparation of N-(4-ethylbenzoyl)-morpholine $N^2$-(3,5-dimethylbenzoyl)$N^2$-t-butylhydrazone a: N-(4-ethylbenzoyl)-morpholine To a cooled solution of 9.6 g (0.11 mole) of morpholine in 25 ml methylene chloride is added 8.4 g (0.05 mole) of 4-ethylbenzoyl chloride dropwise. The reaction is stirred 30 minutes and a white precipitate formed. The mixture is washed three times each with 25 ml of water, dried over anhydrous magnesium sulfate and evaporated in vacuo to yield 10.6 g of yellow oil.

b: N-morpholininum-4-ethylbenzoyl chloride chloride

To a solution of 1.1 g (5.0 mmole) of N-(4-ethylbenzoyl)-morpholine, obtained from Example E.a, in 10 ml of methylene chloride is added 2.5 g (20.0 mmole) of oxalyl chloride. The mixture is stirred one hour then concentrated in vacuo to yield 1 g of a solid residue.

c: N-(4-ethylbenzoyl)-morpholine $N^2$-(3,5-dimethylbenzoyl)-$N^2$-t-butylhydrazone Dissolve 1.0 g (5.0 mmole) of $N^1$-t-butyl-$N^1$-(3,5dimethylbenzoyl)-hydrazine obtained in Example A and 1.0 g (10.0 mmole) of triethylamine in 10 ml methylene chloride and cooled in an ice water bath. To this mixture, add dropwise over 3 minutes a solution of 1.0 g of N-morpholininum-4-ethylbenzoyl chloride chloride obtained in Example E.b in 30 ml of methylene chloride and stirred for 5 minutes. The reaction is washed 3 times each with 50 ml of water, dried over anhydrous magnesium sulfate, concentrated in vacuo and chromatographed on silica in 1:4 ethyl acetate:hexanes to yield the desired product, a pale yellow oil. nmr $(CDC_3)$δ8 1.2 3H t, 1.4 9H s, 2.3 6H s, 2.8 2H q, 3.2 4H bs, 3.6 4H m, 6.6–7.3 7H m.

EXAMPLE F

Preparation of N-(4-ethylbenzoyl)-piperidine $N^2$-(3,5-dimethylbenzoyl)-$N^2$-t-butylhydrazone By substantially following the procedure of Example E, replacing morpholine with piperidine, one obtains the desired product, an off-white solid mp-100°–102° C.

EXAMPLE G

Preparation of N-(4-ethylbenzoyl)-pyrrolidine $N^2$-(3,5-dimethylbenzoyl)-$N^2$-t-butylhydrazone By substantially following the procedure of Example E, replacing morpholine with pyrrolidine, one obtains the desired product, a light yellow solid mp-109°–110° C.

EXAMPLE H

Preparation of 4-Ethylbenzamide $N^2$-(3,5-dimethylbenzoyl)-$N^2$-t-butylhydrazone To 2.7 g of 4-ethylbenzonitrile is added 4.0 g of $N^1$-t-butyl-$N^1$-(3,5dimethylbenzoyl)-hydrazine obtained in Example A and 50 ml of 1-butanol. The resulting mixture is refluxed for 5 hours and concentrated in vacuo yielding a solid which is dissolved in water and extracted with ethyl acetate. The resulting solution is dried over magnesium sulfate and concentrated in vacuo yielding 5.6 g of the desired product, a solid, mp. 90°–96° C.

On the basis of their strong initial pesticidal activity and excellent residual pesticidal activity, compounds according to the invention may be used in low dosages in controlling pests. The amount of dosage depends on a variety of factors, for example, the substance used, the kind of pest, the formulation used, the state of the crop infested with the pest and the prevailing weather conditions. In general, for the control of pests in agriculture and horticulture, a dosage corresponding to from about 0.1 grams to about 1000 grams of the active substance per hectare may be used and from about 5 grams to about 200 grams per hectare of the active substance is preferred. The exact amount of dosage for a given situation can be routinely determined and depends on a variety of factors, for example, the substance used, the kind of pest, the formulation used, the state of the crop infested with the insect and the prevailing weather conditions.

Representative pests which can be controlled by the compounds of the present invention include: American Cockroach (*Periplaneta americana*), Bean Leaf Beetle (*Cerotoma trifurcata*), Bean Leaf Roller (*Urbanus proteus*), Black Carpenter Ant (*Camponotus pennsylvanicus*), Black Cutworm (*Agrotis ipsilon*), Boll Weevil (*Anthonomus grandis grandis*), Colorado Potato Beetle (*Leptinotarsa decemlineata*), Fall Armyworm (*Spodoptera frugiperda*), German Cockroach (*Blattella germanica*), Green June Beetle (*Cotinis nitida*), House Cricket (*Acheta domesticus*), Housefly (*Musca domestica*), Mexican Bean Beetle (*Epilachna varivestis*), Potato Leaf Hopper (*Empoasca fabae*), Red Harvester Ant (*Pogonomyrmex barbatus*), Red Imported Fire Ant (*Solenopsis invicta*), Redlegged Grasshopper (*Melanopus femurrubrum*), Southern Armyworm (*Spodoptera eridania*), Southern Corn Rootworm (*Diabrotica undecimpunctata howardi*), and Tobacco Budworm (*Heliothis virescens*).

It has been found by biological evaluation that compounds according to the present invention have pesticidal activity and are capable of controlling larvae and adult forms of pests, especially insects from the order Lepidoptera. One skilled in the art will know how to determine the activity of a given compound. against a given insect and the dosage required to obtain general or selective pesticidal effects.

What is claimed is:

1. A compound having a formula

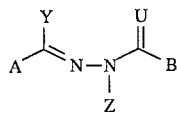

wherein

A is aryl or aromatic heterocyclyl;

B is aryl or aromatic heterocyclyl;

U is oxygen or sulfur;

Y is disubstituted amino ($NR^1R^2$);

wherein $R^1$ and $R^2$ are independently hydrogen, or a substituent selected from W; and W is (alkanoylalkylthio)carbonyl, (alkenylthio)carbonyl, (alkylthio)carbonyl, (alkylthio)thiocarbonyl, (alkynylthio)carbonyl, (phenylalkylthio)carbonyl, alkanoylalkoxycarbonyl, alkanoyloxy, alkenyl, alkenylcarbonyl, alkenyloxy, alkenyloxycarbonyl, alkenylsulfonyl, alkenylthiocarbonyl, alkoxy, alkoxyalkoxy, alkoxyalkoxyalkoxycarbonyl, alkoxyalkoxyalkyl, alkoxyalkoxycarbonyl, alkoxyalkyl, alkoxyalkylcarbonyl, alkoxycarbonyl, alkoxycarbonyl(alkylthio)carbonyl, alkoxycarbonylalkoxycarbonyl, alkoxycarbonylalkyl, alkoxycarbonylalkylthio, alkoxycarbonylcarbonyl, alkoxycarbonyloxy, alkoxycarbonylthio, alkyl, alkylaminocarbonyl, alkylcarbonyl, alkylcarbonyl(alkylthio)carbonyl, alkylcarbonyloxyalkyl, alkylidenedioxy, alkylsulfinyl, alkylsulfinylalkyl, alkylsulfonyl, alkylsulfonyloxy, alkylthio, alkylthioalkoxycarbonyl, alkylthioalkyl, alkylthiocarbonyl, alkynyl, alkynylcarbonyl, alkynyloxy, alkynyloxycarbonyl, alkynylsulfonyl, amino, aromatic heterocyclyl, aryl, carboxy(alkylthio)carbonyl, carboxyalkoxycarbonyl, carboxyalkyl, cyano, cycloalkyl, dialkylphosphoryl, dialkylthiophosphoryl, formamido, formyl, formyloxy, halo, haloalkenyl, haloalkoxy, haloalkyl, halocarbonyl, heterocycyl, hydroxy, hydroxyalkyl, isocyano, N,N-dialkylamino, N,N-dialkylaminocarbonyl, N,N-dialkylaminocarbonylamino, N,N-dialkylaminocarbonyloxy, N,N-dialkylaminosulfonyl, N-(phenylcarbonyl)aminocarbonyl, N-alkoxycarbonyl-N-alkylamino, N-alkylaminocarbonyl, N-alkylaminosulfonyl, N-alkylcarbonyl-N-alkylamino, N-alkylcarbonylamino, N-formyl-N-alkylamino, N-formylamino, N-monoalkylamino, N-monoalkylaminocarbonyl, N-monoalkylaminocarbonylamino, N-monoalkylaminocarbonyloxy, N-monoalkylaminosulfonyl, N-phenyl-N-alkylaminocarbonyl, N-phenylcarbonylamino, naphthyl, nitro, phenyl, phenylalkenylcarbonyl, phenylalkoxy, phenylalkoxycarbonyl, phenylalkyl, phenylalkylcarbonyl, phenylalkylthiocarbonyl, phenylalkynylcarbonyl, phenylcarbonyl, phenyloxy, phenyloxycarbonyl, phenylsulfonyl, phenylthio, phenylthiocarbonyl, pyridyloxy; and Z is a straight or branched ($C_3$–$C_9$)alkyl, optionally substituted with one or two of the same or different ($C_3$–$C_9$)cycloalkyl; and agronomically acceptable diastereomers and enantiomers of such compounds; and agronomically acceptable salts of such compounds.

2. The compound of claim 1 wherein A and B are each phenyl independently unsubstituted or substituted by one to three substituents independently selected from halogens, methyl and ethyl, Z is a branched ($C_4$–$C_7$)alkyl, U is oxygen, and Y is amino, mono($C_1$–$C_3$)alkylamio, or di($C_1$–$C_3$)alkylamino.

3. The compound of claim 2 wherein A is phenyl or 4-ethylphenyl; B is phenyl or 3,5-dimethylphenyl; Y is amino, monomethyamino, or dimethylamino and Z is t-butyl.

4. The compound of claim 3 selected from N-(4-ethylbenzoyl)amine $N^2$-(3,5-dimethylbenzoyl)-$N^2$-t-butylhydrazone and N-(benzoyl)-dimethylamine $N^2$-(3,5-dimethylbenzoyl)-$N^2$-t-butylhydrazone.

5. A composition comprising a pesticidally effective amount of a compound from claim 1 and an inert carrier.

6. An agrochemically acceptable salt of the compound of claim 1.

7. A compound having the formula

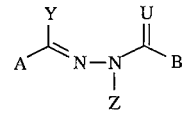

wherein

A is aryl or aromatic heterocyclyl;

B is aryl or aromatic heterocyclyl;

U is oxygen or sulfur

Y is selected from piperidino, morpholino, and pyrrolidino, each of piperidino, morpholino, and pyrrolidino being unsubstituted or substituted with at least one ($C_1$–$C_6$)alkyl; and Z is a straight or branched ($C_3$–$C_9$)alkyl, optionally substituted with one or two of the same or different ($C_3$–$C_9$)cycloalkyl; agronomically acceptable diastereomers and enantiomers of such compounds; and agronomically acceptable salts of such compounds.

8. The compound of claim 7 selected from:

N-(4-bromobenzoyl)-morpholine $N^2$-benzoyl-$N^2$-t-butylhydrazone;

N-(4-bromobenzoyl)-morpholine $N^2$-(3,5-dimethylbenzoyl)-$N^2$-t-butylhydrazone;

N-(4-ethylbenzoyl)-morpholine $N^2$-(3,5-dimethylbenzoyl)-$N^2$-t-butylhydrazone;

N-(4-ethylbenzoyl)-piperidine $N^2$-(3,5-dimethylbenzoyl)-$N^2$-t-butyhydrazone; and N-(4-ethylbenzoyl))-pyrrolidine $N^2$-(3,5-dimethylbenzoyl)-$N^2$-t-butylhdrazone.

9. An agronomically acceptable salt of the compound of claim 7.

10. A method of controlling insects comprising applying an insecticidally effective amount of a compound of claim 1 or 7 to an insect habitat or an insect.

11. The method of claim 10 wherein the insect is from the order Lepidoptera.

* * * * *